(12) United States Patent
Scampini

(10) Patent No.: US 7,508,583 B2
(45) Date of Patent: Mar. 24, 2009

(54) CONFIGURABLE CYTOLOGICAL IMAGING SYSTEM

(75) Inventor: Steven A. Scampini, Boston, MA (US)

(73) Assignee: Cytyc Corporation, Marlborough, MA (US)

( * ) Notice: Subject to any disclaimer, the term of this patent is extended or adjusted under 35 U.S.C. 154(b) by 456 days.

(21) Appl. No.: 11/227,017

(22) Filed: Sep. 14, 2005

(65) Prior Publication Data

US 2007/0057106 A1 Mar. 15, 2007

(51) Int. Cl.
G02B 21/26 (2006.01)
(52) U.S. Cl. ........................................ 359/391; 422/65
(58) Field of Classification Search .......... 359/391–394
See application file for complete search history.

(56) References Cited

U.S. PATENT DOCUMENTS

| | | | | |
|---|---|---|---|---|
| 4,720,463 | A * | 1/1988 | Farber et al. | 435/286.5 |
| 5,386,318 | A * | 1/1995 | Kuhnert et al. | 359/394 |
| 5,700,127 | A * | 12/1997 | Harada et al. | 414/416.08 |
| 6,049,421 | A | 4/2000 | Raz et al. | |
| 6,637,473 | B2 * | 10/2003 | Ganz et al. | 141/130 |
| 6,783,649 | B2 * | 8/2004 | Hedberg et al. | 204/603 |
| 7,006,674 | B1 | 2/2006 | Zahniser et al. | |
| 2003/0179445 | A1 | 9/2003 | Maenle et al. | |
| 2004/0071327 | A1 | 4/2004 | Ellis et al. | |
| 2006/0050376 | A1 * | 3/2006 | Houston et al. | 359/392 |

FOREIGN PATENT DOCUMENTS

| | | |
|---|---|---|
| DE | 4131360 A1 | 3/1993 |
| WO | WO 02/37158 A2 | 5/2002 |
| WO | WO 02/50759 A1 | 6/2002 |
| WO | WO 2005/010495 A2 | 2/2005 |

OTHER PUBLICATIONS

PCT International Search Report for PCT/US2006/034645, Applicant CYTYC Corporation, Forms PCT/ISA/210 and 220, dated Feb. 5, 2007 (6 pages).
PCT Written Opinion of the International Searching Authority for PCT/US2006/034645, Applicant CYTYC Corporation, Form PCT/ISA/237, dated Feb. 5, 2007 (7 pages).
Iqbal Habib, "Automated Microscope Slide Analysis in Pathology", Medical Device Lnk, originally published in IVD Technology, May 2005 (4 pages).

* cited by examiner

Primary Examiner—Stephone B. Allen
Assistant Examiner—Lee Fineman
(74) Attorney, Agent, or Firm—Vista IP Law Group, LLP

(57) ABSTRACT

A configurable slide imaging system includes a plurality of slide cassettes, each cassette configured for accessibly storing a plurality of specimen slides, a plurality of imagers, each operatively coupled with one or more processors for processing images obtained of respective specimen slides retrieved from the storage cassettes, and a slide transport system including a movable arm having a slide engagement mechanism, the slide transport system configured for retrieving slides from the slide cassettes and positioning them on a slide stage of a respective imager, and for retrieving slides from a slide stage of an imager and transporting them to a respective storage cassette. The number of imagers may be selected, and their operation synchronized, so as to minimize down time of the extendable arm 204.

12 Claims, 2 Drawing Sheets

CONFIGURABLE CYTOLOGICAL IMAGING SYSTEM

FIELD OF INVENTION

The present invention pertains generally to systems and methods for screening and reviewing cytological specimens fixed to specimen slides.

BACKGROUND

A typical cytological imaging system, such as the Thin Prep Imaging System manufactured and distributed by Cytyc Corporation (www.cytyc.com), includes an imager having high speed camera that captures on the order of several thousand discrete images of a biological sample fixed on a slide, and a processor which digitizes and processes the captured image data for real time or later analysis. An automated movable arm retrieves individual slides from their respective storage locations in a slide cassette, and positions them (one at a time) on an imaging platform of the imager, at which the images are obtained by the camera. When all of the images from the respective slide are taken and processed, the movable arm returns the slide to its storage location, and retrieves a next slide to repeat the process.

Notably, the movable arm can transport the respective slides from/to the slide cassettes significantly faster than they can be processed by the imager, as the taking and processing a relatively large amount of pictures is relatively slow, tied to both the camera speed and the processing speed of the imager. For example, in a current commercial version of the Thin Prep Imaging System, the imager takes approximately four minutes to acquire and process approximately two-thousand images of each specimen slide. As such, the slide transport movable arm experiences significant down town while each slide is processed.

SUMMARY OF THE INVENTION

In accordance with one embodiment of the invention, a slide imaging system is provided with a plurality of slide cassettes, each cassette configured for accessibly storing a plurality of specimen slides. The imaging system is further provided with a plurality of imagers, each imager operatively coupled with one or more processors for processing images obtained of respective specimen slides retrieved from the storage cassettes. A slide transport system is provided, the slide transport system including a movable arm having a slide engagement mechanism. The slide transport system is configured for retrieving slides from the slide cassettes and positioning them on a slide stage of a respective imager, and for retrieving slides from a slide stage of an imager and transporting them to a respective storage cassette.

The imagers may each have a slide stage upon which a respective slide may be positioned, and a camera configured to capture images of a slide positioned on the slide stage, the respective camera and slide stage of each imager being movable relative to each another. Alternately or additionally, two or more imagers may share a single slide stage, the shared slide stage having at least two slide mounting areas, wherein the at least two imagers are configured to substantially co-temporally capture and process images from respective slides. In some embodiments, at least two of the imagers are mounted one atop the other.

In some embodiments, the movable arm is centrally located relative to the respective slide cassettes and imagers, and is movable in at least three degrees of freedom. For example, in one embodiment, the movable arm is coupled to a vertical track, the at least three degrees of freedom including rotational, axial, and radial movement, respectively, relative to the vertical track.

In other embodiments, the respective slide cassettes and imagers are arranged in a co-planar or roughly co-planar configuration. For example, in one such embodiment, the movable arm is movably coupled to a vertical track, and the vertical track is movably coupled to a horizontal track, such that the movable arm can retrieve and position slides between two or more horizontally displaced components, two or more vertically displaced components, or two or more horizontally and vertically displaced components, where the components are selected from the group consisting of slide cassettes and imagers.

In still other embodiments, the plurality of slide cassettes and imagers are arranged into a first planar or roughly planar array of two or more components, and a second planar or roughly planar array of two or more components. The movable arm is movably coupled to a horizontal track that extends between the respective first and second arrays, such that the movable arm can retrieve and position slides between two or more horizontally displaced components in a same array, or between the arrays, wherein the components are selected from the group consisting of slide cassettes and imagers. In one such embodiment, one or both of the first and second arrays includes at least two vertically mounted components, and wherein the movable arm is movably coupled to a vertical track movably coupled to the horizontal track, such that the movable arm can further retrieve and position slides between two or more vertically displaced components in a same array, or between the arrays.

In yet another embodiment, the configurable slide imaging system comprises a plurality of slide cassettes, each cassette configured for accessibly storing a plurality of specimen slides, and a plurality of imagers, each operatively coupled with one or more processors for processing images obtained of respective specimen slides retrieved from the storage cassettes wherein the at least two of the plurality of imagers are configured to substantially co-temporally capture and process images from respective slides. A slide transport system includes a movable arm movably coupled to a vertical track, the movable arm having a slide engagement mechanism, the slide transport system configured for retrieving slides from the slide cassettes and positioning them on a slide stage of a respective imager, and for retrieving slides from a slide stage of an imager and transporting them to a respective storage cassette.

In still another embodiment, a slide imaging system comprises a plurality of slide cassettes, each cassette configured for accessibly storing a plurality of specimen slides, and a plurality of imagers, each operatively coupled with one or more processors for processing images obtained of respective specimen slides retrieved from the storage cassettes, wherein at least two of the imagers are positioned one atop the other. A slide transport system includes a movable arm movably coupled to a vertical track, the movable arm having a slide engagement mechanism, the slide transport system configured for retrieving slides from the slide cassettes and positioning them on a slide stage of a respective imager, and for retrieving slides from a slide stage of an imager and transporting them to a respective storage cassette. The number of imagers and slide cassettes is configurable, wherein the number of imagers is preferably selected such that, when the system is operating, down time of the movable arm while waiting for slide processing is substantially minimized.

Other and further aspects, features and embodiments of the invention will become apparent from the drawings and following detailed description.

BRIEF DESCRIPTION OF THE DRAWINGS

Embodiments of a configurable imaging system according to the invention are described and schematically depicted in the following detailed description and the accompanying drawings, in which similar elements in alternate embodiments are given common reference numbers, and in which.

DETAILED DESCRIPTION OF THE ILLUSTRATED EMBODIMENTS

Figure 1:
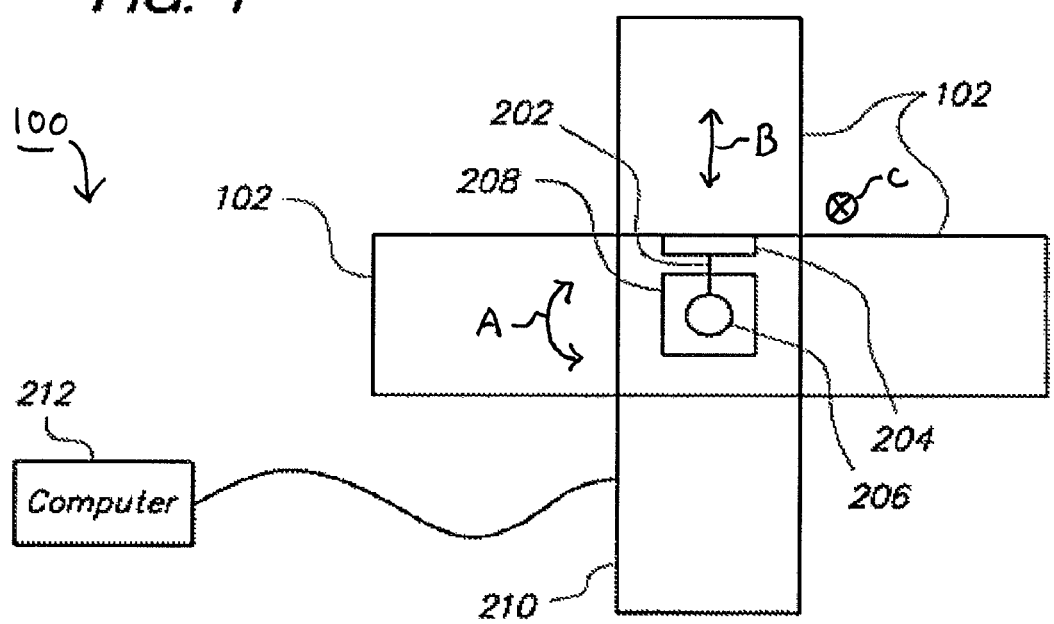
FIG. 1 is a plan view of one embodiment.

FIG. 1 schematically depicts a configurable imaging system 100 according to one embodiment of the invention. The imaging system 100 includes a plurality of slide cassettes 102 (three are shown for ease in illustration) and a plurality of vertically mounted (or stacked) imagers 210 positioned in a generally circumferential pattern around a slide transport assembly 202. The slide transport assembly 202 includes an extendable arm 204 movably coupled to a centrally located vertical track 206. A slide engagement mechanism (not shown) is located at a distal end portion of the extendable arm 204, and is configured to readily engage and disengage individual slides retrieved from the slide cassettes 102.

A drive mechanism 208 is provided for supplying precise movement of the extendable arm 204. The arm 204 is able to rotate about (arrow A in FIG. 1), extend away from, retract towards (arrow B in FIG. 1), and move vertically along (orthogonal direction C to plane of paper in FIG. 1), respectively, the vertical track 206. The slide engagement mechanism can thereby reach any point in three-dimensional space, constrained only by the range of radial extension of the arm 204, and the range of axial (vertical) movement of the arm 204 along the vertical track 206. The drive mechanism 208 can be any known and convenient mechanical and/or electromechanical system for controlling movement of the extendable arm 204 and slide engagement mechanism, including appropriate motor drives (e.g., piezo-electric servo motors) and/or encoders, movable and/or flexible joints, and motion actuation hardware. An exemplary slide transport system utilizing a extendable arm for transporting slides between a storage cassette and an imager is shown and described in U.S. patent application Ser. No. 10/008,379, the contents of which are fully incorporated herein by reference for all that they teach and disclose.

Figure 2:
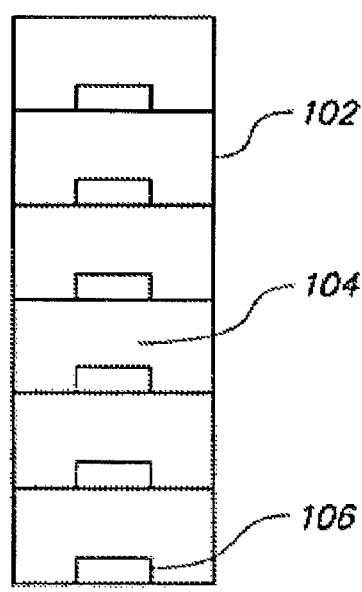
FIG. 2 is an exemplary slide cassette used to store multiple slides in the embodiment of FIG. 1.

An exemplary slide cassette 102 for use in the imaging system 100 is shown in FIG. 2. The slide cassette 102 preferably stores a large number (e.g., at least two dozen) slides 106, which are stacked vertically on individual shelves 104 of the cassette 102. At least one end of the cassette 102 is open to allow access for retrieval and return of the slides 106 from/to the individual shelves 104 by the extendable arm 204. In alternate embodiments, the slide cassettes 102 and/or shelves 104 may have any number of possible configurations, and can be stacked and/or arranged in any convenient pattern allowing for retrieval and return of the slides 106 by the extendable arm 204.

Returning to FIG. 1, the imagers 210 can be implemented as any known and convenient imaging systems and/or mechanisms for capturing discrete, magnified images of specimen samples fixed on the respective slides 106. By way of example, as shown schematically in FIG. 3, each imager 210 preferably includes a slide stage 218, upon which the individual slides 106 are mounted, and a high speed camera 216 positioned to capture images of biological specimens fixed to the slides 106. The slide stage 218 and camera 216 are preferably movable relative to one another so that images of discrete locations on a slide 106 may be obtained. An exemplary imager for use in the imaging system 100 is shown and described in the above-incorporated U.S. patent application Ser. No. 10/008,379. Reference is also made to the teachings and disclosure found in U.S. patent application Ser. No. 09/430,198, the contents of which are fully incorporated herein by reference for all that they teach and disclose.

In alternate embodiments, it may be desirable for two or more imagers 210 to share a single slide stage, wherein the slide stage 218 would have two or more slide mounting areas positioned relative to two or more corresponding cameras 216. Depending on the camera speed relative to the image processing speed, in still further alternate embodiments, a single imager 210 may be equipped with a multi-slide stage 218, wherein a single camera 216 obtains images from two or more slides serially or in parallel. Imagers with still other permutations of cameras and slide stages are also contemplated within the invention.

During operation of the imaging system 100, the slides 106 are retrieved (preferably in a systematic order) one at a time from their respective storage locations (i.e., cassette/shelf 102/104), and positioned on the slide stage 218 of one of the imagers 210 by the extendable arm 204 The imager 210 captures and processes images of the slide specimen, and the slide 106 is removed from the slide stage and returned to its respective storage location by the extendable arm 204. Preferably, this process is continued until all of the specimen slides 106 have been processed.

The imagers 210 are operatively coupled with one or more computers 212 for processing the respective image data. As used herein, "computer" is synonymous with "processor," and there is no requirement that that computer 212 be a component separate from the imager 210, e.g., the imager 210 may be provided with an "internal" processor for performing the image processing. In either case, the imager(s) 210 and/or computer(s) 212 are preferably coupled with an appropriate user interface and image display (neither shown), as a memory having sufficient bandwidth for storing both the system operating software and (at least temporarily) the processed image data from the specimen slides. The imagers 210 and/or computer(s) 212 may be networked, or stand alone. Further, the specimen slide image data may be stored in a local memory associated with the imagers and/or computer(s) 212, or transmitted to another location or storage medium for real-time and later analysis. The slide transport mechanism 202 is preferably controlled by, or otherwise operatively coupled with, the imagers 210 and/or computers 212, in order to synchronize the extendable arm 204 with operation of the various imagers 210.

The actual number of imagers 210 and computers 212 in the system 100 may vary. For example, each imager 210 may have a dedicated computer 212 for processing images, and/or single computer 212 may process images obtained from more than one imager 210, and/or one or more imagers 210 may be linked one or more computers 212, e.g., in a networked configuration, for having images processed by whichever computer 212 has available bandwidth. In preferred embodiments, the image processing bandwidth is modular and configurable, and the number of imagers, computers 212, and associated memory bandwidth is scalable for optimum performance, depending on the number of imagers 210 being supported in parallel.

It will be appreciated that the slide transport mechanism 202 can transport the slides 106 between the respective cassettes 102 and imagers 210 significantly faster than they are processed by the imager 210. For this reason, the number of imagers 210 and image processing computers 212 is preferably sized, and their operation preferably synchronized, such that the extendable arm 204 has minimal down time. In some embodiments, it may be desirable to size and synchronize the system components such that a portion of the available bandwidth of the slide transport system 202 is used to retrieve certain, previously reviewed slides identified by the image processing computer(s) 212 for obtaining and analyzing a second set of images taken by the same or a different imager 210.

Figure 3:
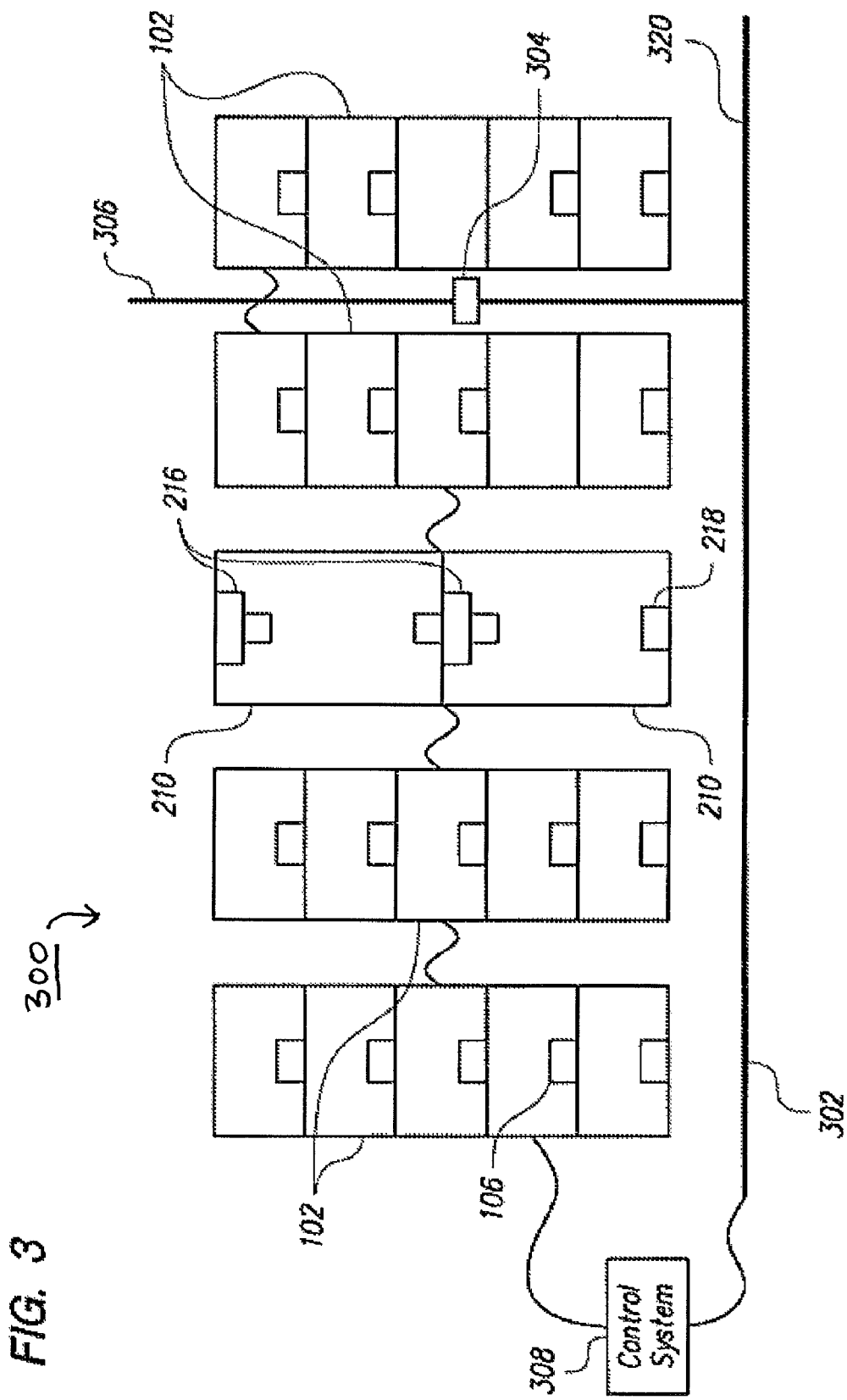
FIG. 3 is an elevation schematic view of an alternate embodiment.

In system 100, the imagers 210 are mounted (or stacked) vertically, i.e., one above the other (best in seen the embodiment of FIG. 3). This allows for efficient use of the extendable arm 204 by moving axially along the vertical track 206, and ease in modularity of the system. For example, a relatively long center rod can accommodate a number of vertically displaced imagers. However, in alternate embodiments, the imagers 210 can be positioned in any convenient pattern relative to each other and the slide cassettes 102, so long as the extendable arm 204 has the necessary access to the respective slide cassettes and imagers 210.

By way of non-limiting examples, one or more of the slide cassettes 102 in the illustrated system 100 can be replaced with an additional imager 210 and/or the slide cassettes 102 can themselves be vertically mounted, and the imagers 210 distributed radially around the extendable arm 204, or both. Thus,. the actual number and physical arrangement of the respective imagers 210 and slide cassettes 102 in the configurable system 100 may be completely modular, and is limited only by the vertical and horizontal reach of the extendable arm 204 for retrieving and returning slides 106. For example, the system 100 may be implemented using a circular array of mounting racks disposed circumferentially about the vertical track 206 of the slide transport mechanism 202. The housing of the respective slide cassettes 102 and imagers 210 can be sized to be substantially identical, or with one being an even multiple of the other, for ease in modularity and incremental sizing of the system 100.

FIG. 3 depicts an alternate embodiment (designated "300") of the configurable imaging system of FIG. 1, in which a plurality (four are shown) of slide cassettes 102 are dispersed in a planar manner, with a pair of vertically mounted imagers 210 positioned proximate a center of the slide cassettes 102. In system 300, the slide transport mechanism 302 is modified from that used in system 100, and includes both a vertical rod (or track) 306 and a horizontal track 320. A extendable arm 304 (similar to extendable arm 204 in system 100) is coupled to, and movable along, the vertical track 306. The vertical track 306, in turn, is coupled to, and is movable along the horizontal track 320.

Movement of the extendable arm 304 in both a radial extension/retraction relative to, and axially along the vertical track 306, is implemented by a slide transport actuation mechanism 308, which also controls horizontal movement of the vertical track 306 along the horizontal track 320. In this manner, a slide engagement mechanism of the extendable arm 304 can reach any point in the planar distribution of the slide cassettes 102 and imagers 210 limited only be the dimensional constraints of the vertical track 306, horizontal track 320, and the extension range of the extendable arm 304.

As with actuation mechanism 208 in system 100, the slide transport actuation mechanism 308 can be any known and convenient mechanical and/or electromechanical system, including an appropriate sizing and arrangement of motor drives and/or encoders and motion actuation hardware.

As in system 100, the imagers 210 in system 300 are operatively coupled with one or more computers (not shown for ease in illustration) for processing the respective image data. Operation of the system 300 is essentially the same as operation of system 100, except that the slide transport system 302 is configured along x and y vertices of a planar configuration. While the imagers 210 in system 300 are mounted vertically, in alternate embodiments, the imagers 210 can be positioned in any convenient pattern or locations relative to each other and the slide cassettes 102, so long as the extendable arm 204 has the necessary access to the respective slide cassettes and imagers 210. By way on non-limiting example, one or more of the slide cassettes 102 can be replaced with an additional imager 210 and/or the slide cassettes 102 can themselves be mounted vertically, the imagers 210 distributed horizontally along the horizontal track 320, or both. Preferably, the imagers are distributed in a pattern along the horizontal track 320 that allows for the most efficient use of the bandwidth of the extendable arm 304, with the actual number and physical arrangement of the respective imagers 210 and slide cassettes 102 in the configurable imaging system 300 being variable and limited only by the vertical, horizontal and lateral reach constraints of the extendable arm 304.

For example, imaging system 300 may be implemented using a side-by-side array of mounting racks disposed along the horizontal track 320 of the slide transport mechanism 302. The housing of the respective slide cassettes 102 and imagers 210 can be sized to be substantially identical, or with one being an even multiple of the other, for ease in modularity and incremental sizing of the system 300. Preferably, the actual number and physical arrangement of the imagers 210 and slide cassettes 102 is selected, and their operation synchronized, such that the extendable arm 304 has minimal down time. In alternate embodiments, it may be desirable to provide a planar distribution of slide cassettes 102 and imagers 210 on both sides of the horizontal track 320, wherein the extendable arm 304 would further be rotabable about the vertical track 306 to move the slides between components located on either side of the horizontal track 320. In yet another alternate embodiment, it may be desirable to provide more than one slide transportation system 202/302 and/or more than one extendable arm 204/304 to increase the slide processing capacity of the system.

It will also be appreciated that embodiments of the invention may include one or more stations configured for mounting or otherwise positioning one or more slides cassettes 102, wherein the user may separately supply slide cassettes. The slide cassettes 102 may themselves be modular, and configured such that they are defined more as a number of shelves 104 than as a number of individual cassettes 106. Further, as used herein, the term "cassette" is not to be defined by any particular housing or structure, but any type of housing or structure suitable for retrievably storing slides may be considered a "cassette. Embodiments of the invention are intended to encompass any type of slide storage structures, in which the individual slides may be retrieved by one or more slide transport mechanisms for imaging at one or more imaging stations. Each of the principal imaging system elements, i.e., slide cassette, imager, image processor and slide transport system of a configurable imaging system according to embodiments of the invention are preferably modular and scalable as to number, size and operational bandwidth.

In the foregoing specification, the embodiments have been described with reference to specific elements thereof. It will, however, be evident that various modifications and changes may be made thereto without departing from the broader scope of the invention, which is to be defined and limited only by the following claims. The specification and drawings are, accordingly, to be regarded in an illustrative rather than restrictive sense.

What is claimed:

1. A slide imaging system, comprising:
   a plurality of slide cassettes, each cassette configured for accessibly storing a plurality of specimen slides;
   a plurality of imagers sharing a single slide stage having at least two slide mounting areas, each imager operatively coupled with one or more processors for processing images obtained of respective specimen slides retrieved from the storage cassettes, wherein the plurality of imagers are configured to substantially co-temporally capture images from respective slides mounted in the single slide stage and wherein at least two of the plurality of imagers are mounted one atop the other; and
   a slide transport system including a movable arm having a slide engagement mechanism, the slide transport system configured for retrieving slides from the slide cassettes and positioning them on the shared slide stage, and for retrieving slides from the shared slide stage and transporting them to a respective storage cassette.

2. The slide imaging system of claim 1, each imager comprising a camera configured to capture images of slides positioned on the shared slide stage, the respective camera and shared slide stage being movable relative to each another.

3. The slide imaging system of claim 1, wherein data from the respective images captured by the at least two imagers is processed substantially simultaneously.

4. The slide imaging system of claim 1, wherein the movable arm is centrally located relative to the respective slide cassettes and imagers, and is movable in at least three degrees of freedom.

5. The slide imaging system of claim 4, wherein the movable arm is coupled to a vertical track, and wherein the at least three degrees of freedom include rotational, axial, and radial movement, respectively, relative to the vertical track.

6. The slide imaging system of claim 1, wherein the respective slide cassettes and imagers are arranged in a co-planar or roughly co-planar configuration.

7. The slide imaging system of claim 6, wherein the movable arm is movably coupled to a vertical track, and the vertical track is movably coupled to a horizontal track, such that the movable arm can retrieve and position slides between two or more horizontally displaced components, two or more vertically displaced components, or two or more horizontally and vertically displaced components, where the components are selected from the group consisting of slide cassettes and imagers.

8. The slide imaging system of claim 1, wherein
   the plurality of slide cassettes and imagers are arranged into a first planar or roughly planar array of two or more components, and a second planar or roughly planar array of two or more components, and
   the movable arm is movably coupled to a horizontal track that extends between the respective first and second arrays, such that the movable arm can retrieve and position slides between two or more horizontally displaced components in a same array, or between the arrays,
   where the components are selected from the group consisting of slide cassettes and imagers.

9. The slide imaging system of claim 8, wherein one or both of the first and second arrays includes at least two vertically mounted components, and wherein the movable arm is movably coupled to a vertical track movably coupled to the horizontal track, such that the movable arm can further retrieve and position slides between two or more vertically displaced components in a same array, or between the arrays.

10. The slide imaging system of claim 1, wherein the respective slide cassettes and imagers are arranged in a co-planar or roughly co-planar configuration, and wherein the vertical track is movably coupled to a horizontal track, such that the movable arm can retrieve and position slides between two or more horizontally displaced components, two or more vertically displaced components, or two or more horizontally and vertically displaced components, wherein the components are selected from the group consisting of slide cassettes and imagers.

11. The slide imaging system of claim 1, wherein the number of imagers and slide cassettes is configurable.

12. The slide imaging system of claim 1, wherein the number of imagers is selected such that, when the system is operating, down time of the movable arm while waiting for slide processing is substantially minimized.

* * * * *